(12) United States Patent
Martin et al.

(10) Patent No.: US 7,928,208 B2
(45) Date of Patent: Apr. 19, 2011

(54) TEMPLATE-SYNTHESIZED DNA NANOTUBES

(75) Inventors: Charles R. Martin, Gainesville, FL (US); Shifeng Hou, Springfield, MO (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 449 days.

(21) Appl. No.: 11/912,902

(22) PCT Filed: May 9, 2006

(86) PCT No.: PCT/US2006/018044
§ 371 (c)(1),
(2), (4) Date: Aug. 18, 2008

(87) PCT Pub. No.: WO2006/122175
PCT Pub. Date: Nov. 16, 2006

(65) Prior Publication Data
US 2009/0299043 A1      Dec. 3, 2009

Related U.S. Application Data

(60) Provisional application No. 60/679,119, filed on May 9, 2005.

(51) Int. Cl.
*C07H 21/04* (2006.01)
*C12Q 1/68* (2006.01)
*C12M 1/36* (2006.01)

(52) U.S. Cl. ............ 536/23.1; 435/6; 435/174; 977/704; 977/742; 977/745; 977/746

(58) Field of Classification Search .................... None
See application file for complete search history.

(56) References Cited

U.S. PATENT DOCUMENTS

| 6,555,362 B2 | 4/2003 | Hidaka et al. |
| 7,162,308 B2 * | 1/2007 | O'Brien et al. ............... 607/116 |
| 7,195,780 B2 * | 3/2007 | Dennis et al. ................ 424/502 |
| 2004/0262636 A1 | 12/2004 | Yang et al. |

OTHER PUBLICATIONS

Hou et al "Layer-by-layer nanotube template synthesis" J. Amer. Chem. Soc. 2004, 126: 5674-5675.*
Moghaddam et al "Highly efficient binding of DNA on teh sidewalls and tips of carbon nanotubes using photochemistry" Nano Letters 2004 4(1): 89-93.*
Keren et al "DNA-templated carbon nanotube fiedl-effect transistor" Science, 2003, 302: 1380-1382.*
Brust M. and Kiely C., "Some recent advances in nanostructure preparation from gold and silver particles: a short topical review," *Colloids and Surfaces A*, Dec. 31, 2002, vol. 202, pp. 175-186.
Cobbe S. et al., "DNA-Controlled Assembly of Protein-Modified Gold Nanocrystals," *Journal of Physical Chemistry B*, 2003, vol. 107, pp. 470-477. "DNA Nanotubes Could Wire Molecular Electronics," Better Humans, Jan. 5, 2004, Abstract only, (http://www.betterhumans.com/News/news.aspx?articleID=2004-01-05-4).
Hou, Shifeng, et al., "Template-Synthesized DNA Nanotubes," *Journal of the American Chemical Society*, 2005, vol. 127, No. 24, pp. 8586-8587.
O'Neill, Patrick, "Sturdier DNA nanotubes via litigation," Meeting of the American Physical Society, Mar. 2005 Meeting, Abstract only, (http://meetings.aps.org/Meeting/MAR05/Event/23575).

* cited by examiner

*Primary Examiner* — B J Forman
(74) *Attorney, Agent, or Firm* — Saliwanchik, Lloyd & Eisenschenk

(57) ABSTRACT

A method of forming DNA nanotubes composed entirely or predominantly from DNA that, The methods of the present invention form single layer or multilayer template-synthesized nanotubes where the bulk of the tube is composed of DNA, and the layers are held together by hybridization of complementary DNA strands. The DNA molecules making up these tubes may be varied as desired, and the DNA is capable of being released from the tube.

16 Claims, 3 Drawing Sheets

SEQUENCE LISTING

```
<160> NUMBER OF SEQ ID NOS: 7

<210> SEQ ID NO 1
<211> LENGTH: 18
<212> TYPE: DNA
<213> ORGANISM: Artificial Sequence
<220> FEATURE:
<223> OTHER INFORMATION: DNA sequence synthesized to form an inner layer
      of a nanotube

<400> SEQUENCE: 1
tttggagtga cctggtgt                                                          18

<210> SEQ ID NO 2
<211> LENGTH: 30
<212> TYPE: DNA
<213> ORGANISM: Artificial Sequence
<220> FEATURE:
<223> OTHER INFORMATION: DNA sequence synthesized to form a second layer
      of a nanotube

<400> SEQUENCE: 2
cctcactgga ccacacgcat tcagccttct                                             30

<210> SEQ ID NO 3
<211> LENGTH: 30
<212> TYPE: DNA
<213> ORGANISM: Artificial Sequence
<220> FEATURE:
<223> OTHER INFORMATION: DNA sequence synthesized to form a third layer
      of a nanotube

<400> SEQUENCE: 3
gcgtaagtcg gaagagtagt gacctggtgt                                             30

<210> SEQ ID NO 4
<211> LENGTH: 30
<212> TYPE: DNA
<213> ORGANISM: Artificial Sequence
<220> FEATURE:
<223> OTHER INFORMATION: DNA sequence synthesized to form a fourth layer
      of a nanotube

<400> SEQUENCE: 4
catcactgga ccacacgcat tcagcattct                                             30

<210> SEQ ID NO 5
<211> LENGTH: 30
<212> TYPE: DNA
<213> ORGANISM: Artificial Sequence
<220> FEATURE:
<223> OTHER INFORMATION: DNA sequence synthesized to form a fifth layer
      of a nanotube

<400> SEQUENCE: 5
gcgtaagtcg taagagtagt gacctggtgt                                             30

<210> SEQ ID NO 6
<211> LENGTH: 24
<212> TYPE: DNA
```

```
<213> ORGANISM: Artificial Sequence
<220> FEATURE:
<223> OTHER INFORMATION: DNA sequence synthesized to form a second layer
      of a nanotube

<400> SEQUENCE: 6
cactggacca caattcagcc ttct                                              24

<210> SEQ ID NO 7
<211> LENGTH: 24
<212> TYPE: DNA
<213> ORGANISM: Artificial Sequence
<220> FEATURE:
<223> OTHER INFORMATION: DNA sequence synthesized to form a third layer
      of a nanotube

<400> SEQUENCE: 7
taagtcggaa gagtgacctg gtgt                                              24
```

TEMPLATE-SYNTHESIZED DNA NANOTUBES

CROSS-REFERENCE TO RELATED APPLICATIONS

This application is a National Stage Application of International Application Number PCT/US2006/018044, filed May 9, 2006; which claims priority to U.S. Provisional Application Ser. No. 60/679,119, filed May 9, 2005.

GOVERNMENT SUPPORT

The subject matter of this application has been supported by a research grant from the National Science Foundation, NSF Grant No.: EEC 02-10580. Accordingly, the government has certain rights in this invention.

BACKGROUND OF INVENTION

The emerging field of molecular electronics has made considerable recent progress in the development of molecular-scale electronics components and sensors, but the need for templating and patterning at the molecular scale is a major challenge. One approach is the use of DNA-based nanotechnology, which seeks to engineer synthetic DNA polymers to encode information necessary for realization of desired structures or processes on the molecular level.

In addition, there is considerable interest in DNA-functionalized nanotubes with proposed applications that include use as gene delivery vehicles in DNA-assisted separation and assembly of carbon nanotubes, and in nanotube-based DNA sensing and separations. In previous prior art methods, individual DNA molecules were attached to a substrate composed of a second material.

In one such prior art method, the DNA was attached to a nanotube composed of a second material. In one example, DNA-functionalized nanotube membranes have been used wherein DNA is attached to a nanotube membrane that may be composed of gold or carbon. However, these nanotubes only have DNA molecules in selected locations of the nanotube, thereby limiting the effectiveness of the nanotubes.

In another prior art aspect, a self-assembling superstructure is composed of DNA tiles. Double- or triple-crossover tiles modified with thiol-containing double-stranded DNA stems projecting out of the tile plane have been developed and used as basic building blocks. However, these methods are complex and still may not result in a DNA nanotube composed entirely or predominantly from DNA.

Accordingly, it would be beneficial to provide a system and method for forming nanotubes composed entirely or predominantly from DNA. It would also be beneficial to provide a template synthesis method of forming DNA nanotubes that enable the DNA nanotubes to be composed entirely or predominantly from DNA.

BRIEF SUMMARY

The present invention provides a system and method for forming DNA nanotubes. The system and method involve the use of a template synthesis method to form the DNA nanotubes. The systems and methods of the present invention form single layer or multilayer template-synthesized nanotubes where the bulk of the tube is composed of DNA, and the layers are held together by hybridization of complementary DNA strands. The DNA molecules making up these tubes may be varied as desired, and the DNA is capable of being released from the tube. The resulting DNA nanotubes have a wide variety of uses, such as for gene delivery vehicles, in DNA-assisted separation and assembly of carbon nanotubes, and/or in nanotube-based DNA sensing and separations.

In one aspect, the present invention provides a DNA nanotube including a nanotube template, and DNA material attached to the nanotube template. In additional embodiments, a bonding layer may be attached to the nanotube template to which the DNA material is attached. In another aspect, the present invention provides a method of forming DNA nanotubes including the steps of providing a nanotube template and attaching a first DNA material to the nanotube template. In additional embodiments, the method may include the steps of attaching a bonding layer to the nanotube template to which the DNA material is then attached.

BRIEF DESCRIPTION OF DRAWINGS

Other objects, features and advantages of the present invention will become apparent upon reading the following detailed description, while referring to the attached drawings, in which.

BRIEF DESCRIPTION OF THE SEQUENCES

Figure 1:
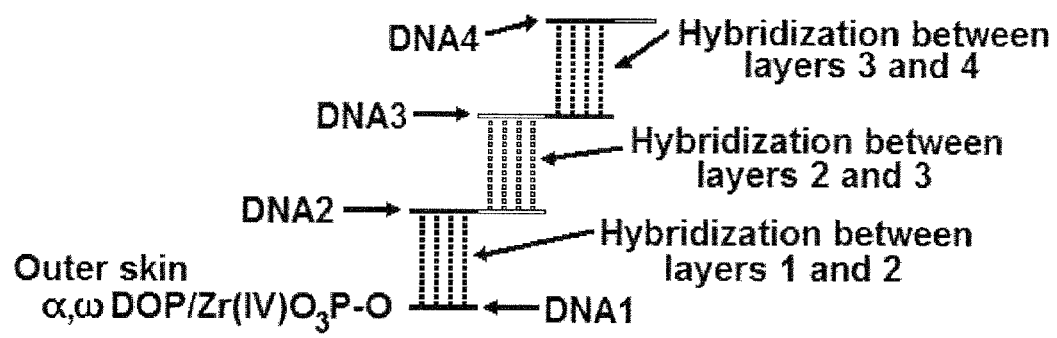
FIG. 1 provides an example of a multi-layer DNA nanotube construction according to one embodiment of the present invention.

SEQ ID NO:1 is a synthetic DNA sequence used to form an inner layer of a nanotube in one embodiment of the invention.

SEQ ID NO:2 is a synthetic DNA sequence used to form a second layer of a nanotube in one embodiment of the invention.

SEQ ID NO:3 is a synthetic DNA sequence used to form a third layer of a nanotube in one embodiment of the invention.

SEQ ID NO:4 is a synthetic DNA sequence used to form a fourth layer of a nanotube in one embodiment of the invention.

SEQ ID NO:5 is a synthetic DNA sequence used to form a fifth layer of a nanotube in one embodiment of the invention.

SEQ ID NO:6 is a synthetic. DNA sequence used to form a second layer of a nanotube in one embodiment of the invention.

SEQ ID NO:7 is a synthetic DNA sequence used to form a third layer of a nanotube in one embodiment of the invention.

DETAILED DISCLOSURE

The present invention is more particularly described in the following description and examples that are intended to be illustrative only since numerous modifications and variations therein will be apparent to those skilled in the art. As used in the specification and in the claims, the singular form "a," "an," and "the" may include plural referents unless the context clearly dictates otherwise. Also, as used in the specification and in the claims, the term "comprising" may include the embodiments "consisting of" and "consisting essentially of."

The present invention provides a method of forming DNA nanotubes composed entirely or predominantly from DNA.

The present invention provides a new family of layer-by-layer template-synthesized nanotubes where the bulk of the tube is composed of DNA, and the layers are held together by hybridization of complementary DNA strands. The DNA molecules comprising these tubes may be varied at will, and the DNA may be released from the tube by melting of the duplexes.

The DNA nanotubes produced in the present invention may be formed using a template synthesis method. In this method, tubes of the selected DNA material are deposited along the walls of the pores of a nanopore template membrane. Essentially, the template acts as a skeleton for the nanoscale synthesis and macroscale contact of the DNA. One advantage of the template method is that nanotubes composed of nearly any selected material may be prepared. Hence, with template synthesis is effective at forming DNA nanotubes wherein the nanotubes are composed almost entirely of DNA.

In the methods of the present invention, the systems and methods use nanotube templates. Nanotubes are tiny cylinder-shaped structures (a nanometer is one millionth of a millimeter). The nanotube templates may be composed of a variety of different materials. The nanotubes used in the present invention may be any material capable of permitting one or more layers of DNA material to be attached thereto. Examples of materials useful in the present invention include, but are not limited to, carbon, gold, or other metals, inorganic materials such as silica or alumina, or a combination thereof. In particularly select embodiments of the present invention, the nanotube templates are alumina template membranes.

The size of the nanotubes formed in the present invention may vary depending on the size of the number of DNA layers, the size of the target molecule, the material used for the nanotube template, or a combination thereof. In one embodiment, the size of the DNA nanotubes is from about 1 to about 100 nm. In another embodiment, the size of the DNA nanotubes is from about 5 to about 20 nm. In another embodiment, the size of the DNA nanotubes is from about 10 to about 15 nm.

In addition to the nanotube template, the methods of the present invention may also utilize a bonding layer that bonds to the nanotube template and to which the DNA material bonds. The methods of the present invention may use any bonding layer that is capable of bonding to a nanotube template and that is capable of bonding to a layer of DNA material. In one embodiment, the present invention is based upon a synthetic strategy that builds on prior art systems wherein alternating $\alpha,\omega$-diorganophosphonate ($\alpha,\omega$-DOP) Zr(IV) chemistry is used to deposit layered nanotubes along the pore walls of an alumina template membrane. In this embodiment, the bonding layers are held together by bonds between the phosphonate groups and the Zr(IV) ions, and the polyvalency of this interaction provides crosslinking that imparts structural integrity to these layered nanotubes. The DNA nanotubes of the present invention have, in one embodiment, an outer skin of one or more of these $\alpha,\omega$-DOP/Zr(IV) bonding layers, again to provide structural integrity, surrounding an inner core of one or more multiple double-stranded DNA layers held together by hybridization between the layers. This may be seen in greater detail in FIG. 1.

In addition to the nanotube templates and the bonding layer, the present invention includes one or more DNA materials that may be added in layers, either to the nanotube template directly or via attachment to the bonding layer. As such, the DNA nanotubes of the present invention may be composed of one layer of DNA material, or, in alternative embodiments, may have 2, 3, 4, or more layers of DNA material. In the multi-layer embodiments, each layer of DNA may be held to the adjacent layer through hybridization of the two DNA layers. In these embodiments, base segments within each DNA layer are hybridized (double-stranded) with base segments of the adjacent DNA layer. In one embodiment, the base segments are from about 5 to about 50 bases in length. In another embodiment, the base segments are from about 8 to about 20 bases in length. In yet another embodiment, the base segments are from about 12 to about 15 bases in length. It is to be understood that the length of the base segments that may be hybridized may be shorter than 5 bases or longer than 50 bases and that any length is sufficient provided the base segment is capable of hybridizing with another base segment to join two DNA layers to one another.

The DNA nanotubes of the present invention may be used in a wide variety of processes, such as for gene delivery vehicles, in DNA-assisted separation and assembly of carbon nanotubes, and/or in nanotube-based DNA sensing and separations. In each of these methods, the DNA nanotubes may be used with a particular DNA layer that is complimentary to a selected target DNA molecule.

Accordingly, for DNA-assisted separation and/or DNA sensing, the DNA nanotube is capable of binding to a target molecule for separating the target molecule from a solution and/or detecting the presence of the target molecule in the solution.

In regards to gene delivery vehicles, the DNA nanotube may have the target molecule attached thereto and may then be placed in a location of interest and the target molecule is released to thereby deliver the target molecule to the selected location.

Once the selected target molecule has been attached to the DNA nanotube, the target molecule may be caused to be released from the DNA nanotube, such as to deliver the target molecule to a selected location or to permit reuse of the DNA nanotube. In one embodiment, the target molecule may be caused to be released from the DNA nanotube through thermal decomposition. In this embodiment, the nanotube is heated to a temperature sufficient to cause decomposition of the bonds between the DNA nanotube and the target molecule. The temperature at which the thermal decomposition may vary depending on one or more factors including, but not limited to, the characteristics of the DNA nanotube, the target molecule, and/or whether the DNA nanotube is being used for gene delivery. In one embodiment, the DNA is heated to a temperature of from about 50 to about 100° C.

In addition to thermal decomposition, any method capable of causing a break down of the bonds between the DNA nanotube and the target molecule may be used in the present invention to cause delivery of the target molecule to a selected location and/or to permit reuse of the DNA nanotube.

In an alternative embodiment, and in those embodiments wherein the DNA nanotubes have multiple DNA layers, thermal decomposition or any other capable method may also be used to cause dehybridization between the different DNA layers to permit one or more layers of the DNA to be removed.

Reference will now be made to different embodiments and examples wherein the versatility of the device of the present invention may be better understood. However, it is to be understood that these embodiments are for example purposes only and are not to be considered to be limiting in any manner of the overall scope of the present invention.

EXAMPLES

Example 1

The template membrane was a nanopore alumina, 36 µm thick, and 1 cm² area, with ~100 nm-diameter pores. Both faces of the membrane were first sputtered with a ~5 nm film of Au. The outer α,ω-DOP/Zr(IV) nanotube skin was prepared by immersing the membrane into a 1.25 mM solution of 1,10-decanediylbis (phosphonic acid) (the α,ω-DOP), and then into a 5.0 mM solution of $ZrOCl_2$. While DNA nanotubes with an outer skin including only one such α,ω-DOP/Zr(IV) layer were used for most of the studies described herein, analogous data were obtained for DNA tubes with 3-layer α,ω-DOP/Zr(IV) outer skins.

The DNA core that makes up the majority of the nanotube was then synthesized within this α,ω-DOP/Zr(IV) skin. A 1 M NaCl solution that was 50 μM in both DNA 1 (5'-($H_2O_2PO$)-TTT-GGA-GTG-ACC-TGG-TGT-3'; SEQ ID NO:1) and DNA 2 (3'-CCT-CAC-TGG-ACC-ACA-CGC-ATT-CAG-CCT-TCT-5'; SEQ ID NO:2) (FIG. 1) was prepared, and 24 hrs were allowed for the two 15-base segments shown in bold font to hybridize. The membrane containing the α,ω-DOP/Zr(IV) skin was then immersed into this solution for 30 hrs to allow the phosphonate end of DNA 1 to bind to the Zr(IV) on the inner surface of the skin. This resulted in a nanotube composed of (from outer to inner layer) α,ω-DOP/Zr(IV)/DNA 1/DNA 2—a 2-layer DNA nanotube. To make a 3-layer DNA nanotube, this membrane was subsequently immersed into an analogous solution of DNA 3 (5'-GCG-TAA-GTC-GGA-AGA-GTA-GTG-ACC-TGG-TGT-3'; SEQ ID NO:3). This resulted in hybridization of the 15-base segments of DNA 2 and DNA 3 (green font in FIG. 1) to yield a nanotube composed of α,ω-DOP/Zr(IV)/DNA 1/DNA 2/DNA 3. DNA 4 (3'-CAT-CAC-TGG-ACC-ACA-CGC-ATT-CAG-CAT-TCT-5'; SEQ ID NO:4) and DNA 5 (5'-GCG-TAA-GTC-GTA-AGA-GTA-GTG-ACC-TGG-TGT-3'; SEQ ID NO:5) were subsequently added to make the 4- and 5-layer nanotubes. The DNA layers in these tubes were held together by hybridization between DNA segments that are 15 bases long.

Figure 2:
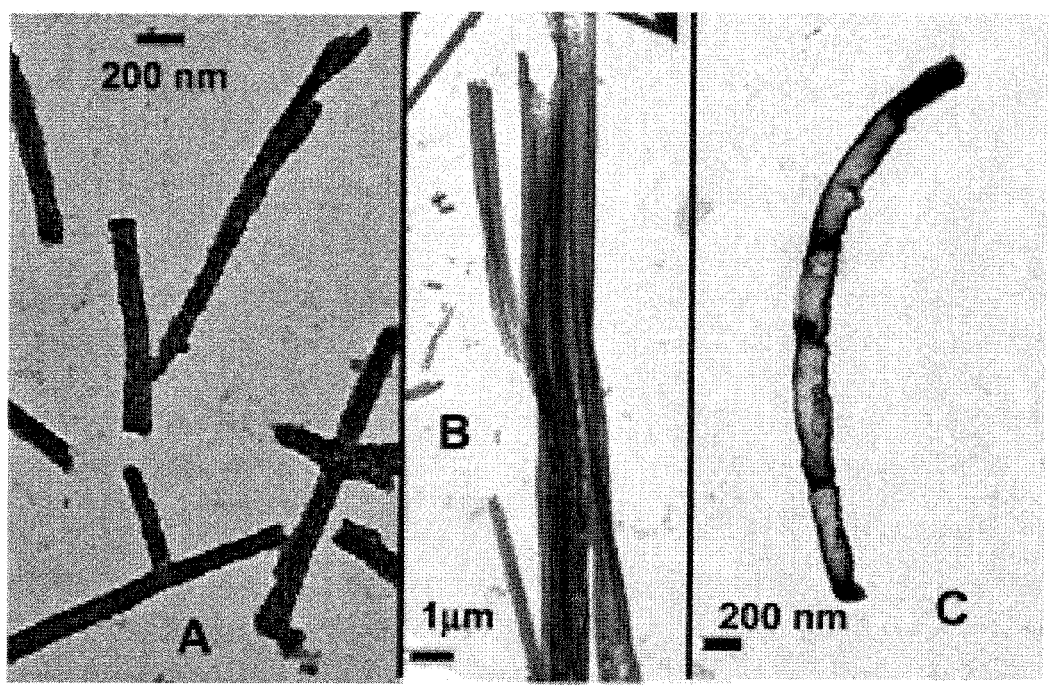
FIGS. 2A-C are transmission electron micrograph (TEM) images of 5-layer DNA nanotubes according to one embodiment of the present invention.

The nanotubes were liberated by dissolution of the template in a solution that was 1.5% in $H_3PO_4$ and 2M in NaCl at 0° C.—and collected by centrifugation. The high salt content and low temperature were used to help insure that dehybridization did not occur during membrane dissolution. FIG. 2A shows a transmission electron micrograph (TEM) of liberated 5-layer DNA nanotubes that had an outer skin of only one α,ω-DOP/Zr(IV) layer. The nanotube length is much shorter than the thickness of the template. This indicated that the nanotubes were broken during membrane dissolution and centrifugation. This problem can be mitigated by preparing nanotubes with outer skins that are three, α,ω-DOP/Zr(IV) layers thick or more. Because this outer skin provides structural integrity, these thicker-skinned nanotubes are less susceptible to breakage, which may be seen in FIG. 2B.

Because these nanotubes were held together by hybridized DNA chains (FIG. 1), heating the tubes above the melting point of the dsDNA was used to release the dehybridized ssDNA chains from the tubes; i.e., thermal decomposition provided a route for releasing the "DNA payload" from these nanotubes. A TEM provided the first evidence that his occurred. FIG. 2C chows an image of a DNA nanotube identical to that in FIG. 2A, but after heating in a buffer solution at 85° C. While the nanotubes that had not been heated are electron opaque (FIG. 2A), the heated nanotube is nearly electron transparent (FIG. 2C). This is because the DNA payload has been released, and this "ghost" tube included only the outer α,ω-DOP/Zr(IV) skin.

To explore this issue quantitatively, samples of DNA-nanotube-containing alumina membranes were immersed into buffer solution and heated from 23° C. to 85° C. Because the nanotubes were sequestered within the pores of the template, there was initially no DNA present in the solution. However, melting of the dsDNA duplexes released the component ssDNA chains into the solution, where they were detected by UV absorbance (260 nm). Analogous data were obtained for nanotubes that had been liberated from the template membrane. In this case, the nanotubes were present as a compacted film on the bottom of the centrifuge tube. Buffer was added, and the UV absorbance of the solution above this compacted film was measured as a function of temperature.

Figure 3:
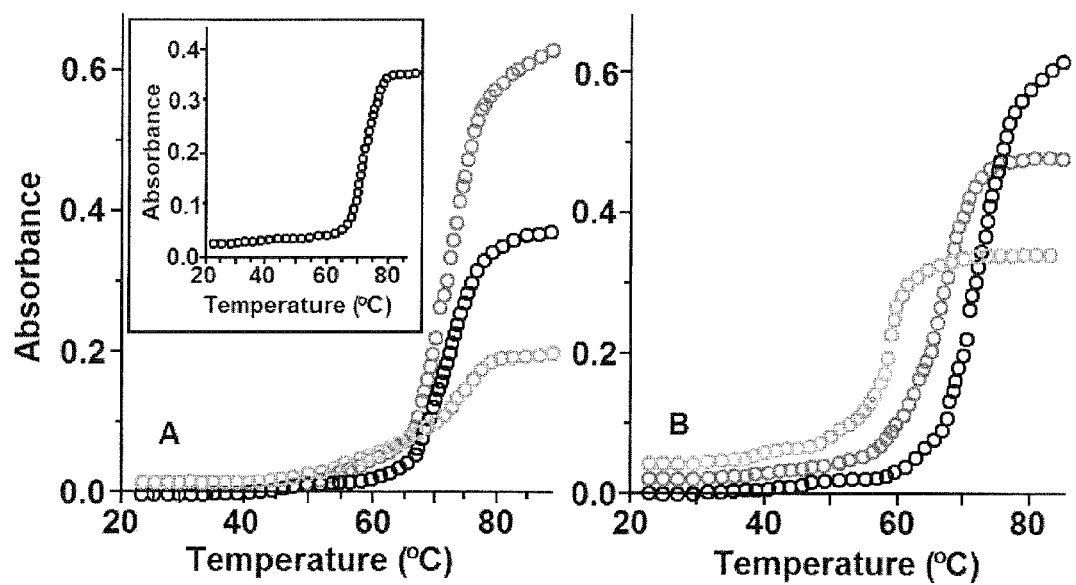
FIGS. 3A-B are thermal decomposition curves for A) Nanotubes composed of the DNAs in FIGS. 1 and B) 5-layer nanotubes composed of hybridized 8-base, 12-base and 15-base duplexes.

FIG. 3A shows thermal decomposition curves for 2-, 3-, and 5-layer DNA nanotubes (outer skin=one α,ω-DOP/Zr(IV) layer) that were sequestered within the pores of the template membrane. At lower temperatures, no DNA was present in the solution above the membrane, and at higher temperatures DNA was released with a temperature profile similar to that of a DNA melting curve. Indeed, the duplexes obtained by hybridizing the various 15-base segments in FIG. 1 had calculated melting temperatures ($T_m$) between about 70° C. and 74° C. Correspondingly, the thermal decomposition curves in FIG. 3A had temperatures at half maxima (apparent $T_m$, $T_{m,app}$) of ~73° C. $T_{m,app}$ values for nanotubes that were liberated from the template were identical, which may be seen in the inset in FIG. 3A.

The surface coverage of 21-mer DNA duplexes on a nanopore alumina like that used here was found to be $3 \times 10^{12}$ per $cm^2$. Densities on other surfaces were nearly identical. From this number, and the total surface area of the template, it was calculated that ~2.7 nmoles of DNA 2 were present in 1 $cm^2$ of the 2-layer DNA nanotube membrane; 1.9±0.2 nmoles were obtained experimentally. Also, the quantity released from the 3-layer nanotubes was about twice that from the 2-layer tubes, and an experimental ration of 1.9 was obtained, which may be seen in FIG. 3A.

Thermal decomposition data were also obtained for nanotubes where the DNA layers were held together by hybridized chain segments 12- and 8-bases long (FIG. 3B). In both cases the nanotubes were five DNA layers thick, and the first DNA layer was DNA 0.1 (FIG. 1). To make nanotubes held together by hybridized 12-base segments, the second layer was the sequence 3'-CAC-TGG-ACC-ACA-ATT-CAG-CCT-TCT-5'; SEQ ID NO:6, which was called DNA 6. Because the first 12 bases at the 3' end of DNA 6 are complementary to the last 12 bases at the 3' of DNA 1, DNA 1 and DNA 6 form a 12-base duplex. The third layer was 5'-TAA-GTC-GGA-AGA-GTG-ACC-TGG-TGT-3'; SEQ ID NO:7 and was called DNA 7. The fourth layer was DNA 6, and the fifth layer was DNA 7. A similar route was used to prepare the nanotubes held together by hybridization between segments 8-bases long.

FIG. 3B compares thermal decomposition curves for 5-layer DNA nanotubes where the layers were held together by duplexes 8-, 12-, and 15-bases long. The $T_{m,app}$ values obtained from these curves were 8-base=55° C., 12-base –62° C., and 15-base=73° C. These $T_{m,app}$ values were in good agreement with calculated Tm values for the various duplexes comprising these DNA nanotubes. Finally, FIG. 3B also shows, as expected, that the total quantity of oligonucleotide released increases with the length of the DNA chains comprising the nanotubes.

It is to be understood that while the invention has been described in conjunction with the specific embodiments thereof, that the foregoing description as well as the examples which follow are intended to illustrate and not limit the scope of the invention. Other aspects, advantages and modification within the scope of the invention will be apparent to those skilled in the art to which the invention pertains.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A DNA nanotube comprising;
an outer skin comprising at least one bonding layer; and
DNA material attached to the bonding layer, wherein the DNA material is the core of the DNA nanotube, and wherein the bonding layer comprises at least one α,ω-diorganophosphonate Zr(IV) layer.

2. The DNA nanotube of claim 1, wherein the DNA material comprises at least two layers of DNA material, and wherein each layer of DNA material is attached to an adjacent DNA layer through hybridization.

3. The DNA nanotube of claim 2, wherein the hybridization occurs between base segments that are from about 5 to about 50 bases in length.

4. The DNA nanotube of claim 2, wherein the hybridization occurs between base segments that are from about 8 to about 15 bases in length.

5. The DNA nanotube of claim 1, further comprising a nanotube template attached to the bonding layer that is attached to the DNA material.

6. The DNA nanotube of claim 5, wherein the nanotube template is composed of a material selected from carbon, gold, silica, alumina, or a combination thereof.

7. The DNA nanotube of claim 6, wherein the nanotube template is composed of alumina.

8. The DNA nanotube of claim 1, wherein the bonding layer comprises a plurality of α,ω-diorganophosphonate Zr(IV) layers.

9. A method of forming DNA nanotubes comprising:
providing a nanotube template;
attaching to the nanotube template at least one bonding layer comprising at least one α,ω-diorganophosphonate Zr(IV) layer; and
attaching a DNA material to the bonding layer, wherein the DNA material forms the core of the DNA nanotube.

10. The method of claim 9, wherein the nanotube template is composed of a material selected from carbon, gold, silica, alumina, or a combination thereof.

11. The method of claim 10, wherein the nanotube template is composed of alumina.

12. The method of claim 9, further comprising removing the nanotube template.

13. The method of claim 9, wherein the bonding layer comprises a plurality of α,ω-diorganophosphonate Zr(IV) layers.

14. The method of claim 9, wherein attaching a DNA material comprises
attaching at least two layers of DNA material, wherein each layer of DNA material is attached to an adjacent DNA layer through hybridization.

15. The method of claim 14, wherein the hybridization occurs between base segments that are from about 5 to about 50 bases in length.

16. The method of claim 15, wherein the hybridization occurs between base segments that are from about 8 to about 15 bases in length.

* * * * *

UNITED STATES PATENT AND TRADEMARK OFFICE
CERTIFICATE OF CORRECTION

Page 1 of 1

PATENT NO.         : 7,928,208 B2
APPLICATION NO.    : 11/912902
DATED              : April 19, 2011
INVENTOR(S)        : Charles R. Martin and Shifeng Hou It is certified that error appears in the above-identified patent and that said Letters Patent is hereby corrected as shown below:

<u>On the Title Page Item (57) Abstract,</u>
Line 2, "DNA that, The" should read --DNA that the--.

<u>Column 2,</u>
Line 49, "synthetic. DNA" should read --synthetic DNA--.

<u>Column 5,</u>
Lines 56-57, "that his occurred. Figure 2C chows an image" should read --that this occurred. Figure 2C shows an image--.

<u>Column 6,</u>
Line 40, "DNA 0.1" should read --DNA 1--.

Signed and Sealed this
Nineteenth Day of July, 2011

David J. Kappos
*Director of the United States Patent and Trademark Office*